United States Patent [19]

Logue

[11] Patent Number: 5,754,043

[45] Date of Patent: May 19, 1998

[54] DRIVING CORES FOR POLAR COORDINATES SENSORS

[76] Inventor: Delmar L. Logue, R. R. #1, Box 60, Herrick, Ill. 62431

[21] Appl. No.: 685,854

[22] Filed: Jul. 24, 1996

Related U.S. Application Data

[63] Continuation-in-part of Ser. No. 142,933, Oct. 29, 1993, Pat. No. 5,532,591, Ser. No. 187,072, Jan. 27, 1994, Pat. No. 5,547,367, Ser. No. 217,738, Mar. 25, 1994, Pat. No. 5,554,933, Ser. No. 267,511, Jun. 29, 1994, Pat. No. 5,559,432, Ser. No. 388,825, Feb. 15, 1995, Pat. No. 5,548,212, and Ser. No. 599,775, Feb. 12, 1996.

[51] Int. Cl.$^6$ .............. G01N 27/72; G01B 7/00; G01R 33/00
[52] U.S. Cl. .......... 324/207.26; 324/228; 324/232; 324/239; 324/240
[58] Field of Search .......... 324/207.17–207.19, 324/207.26, 228, 232, 239–243

[56] References Cited

U.S. PATENT DOCUMENTS

| | | |
|---|---|---|
| 3,876,932 | 4/1975 | Domon et al. ............. 324/232 X |
| 4,595,843 | 6/1986 | Del Vecchio et al. . |
| 5,404,101 | 4/1995 | Logue ..................... 324/207.17 |

FOREIGN PATENT DOCUMENTS

| | | | |
|---|---|---|---|
| 29253 | 3/1977 | Japan | ............. 324/209 |

Primary Examiner—Gerard R. Strecker

[57] ABSTRACT

An elongated hollow toroid driving core having a pick-up core formed as an integral part. A cross shaped driving core having two orthogonal sine-cosine excited flux circuits, a polar sensor is mounted where the cross arms intersect, the axis of the polar sensor being perpendicular to the driving core surface, thus disposing the winding turns of the pick-up coil coplanar to the driving flux lines. A third embodiment of a driving core device includes a hollow toroid and cross shaped driving core combination providing dual interacting rotating fields generating a sensing pattern having additive or subtractive dipoles that may be steerable.

7 Claims, 6 Drawing Sheets

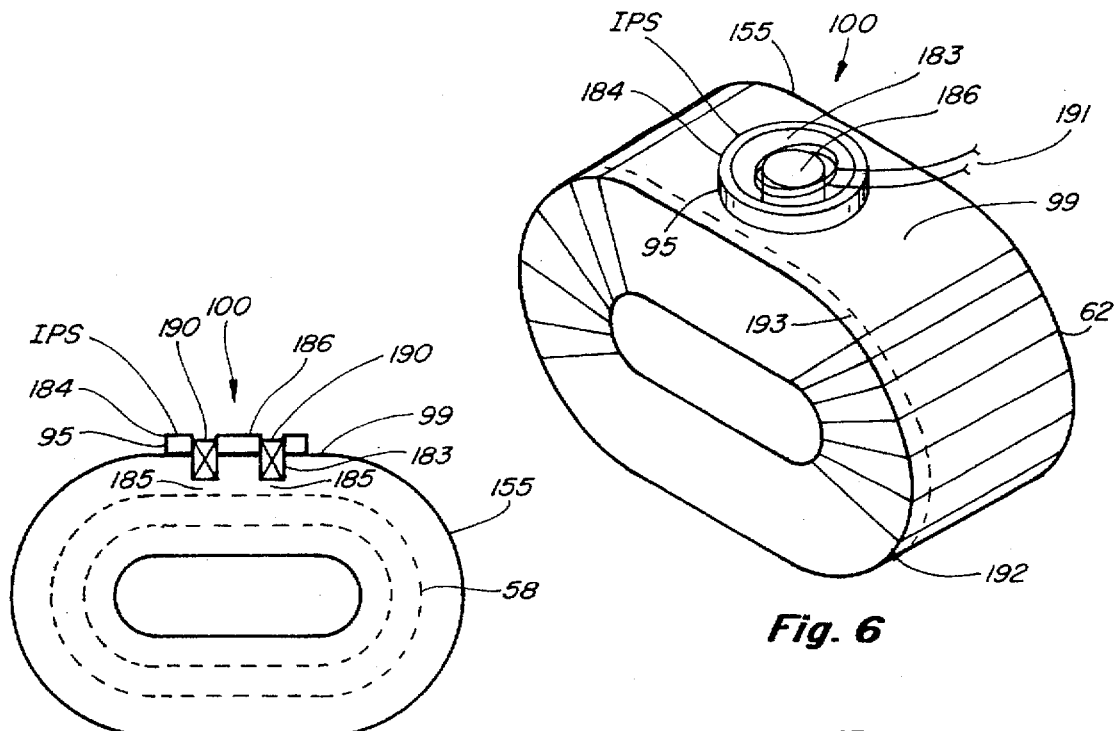
*Fig. 6*
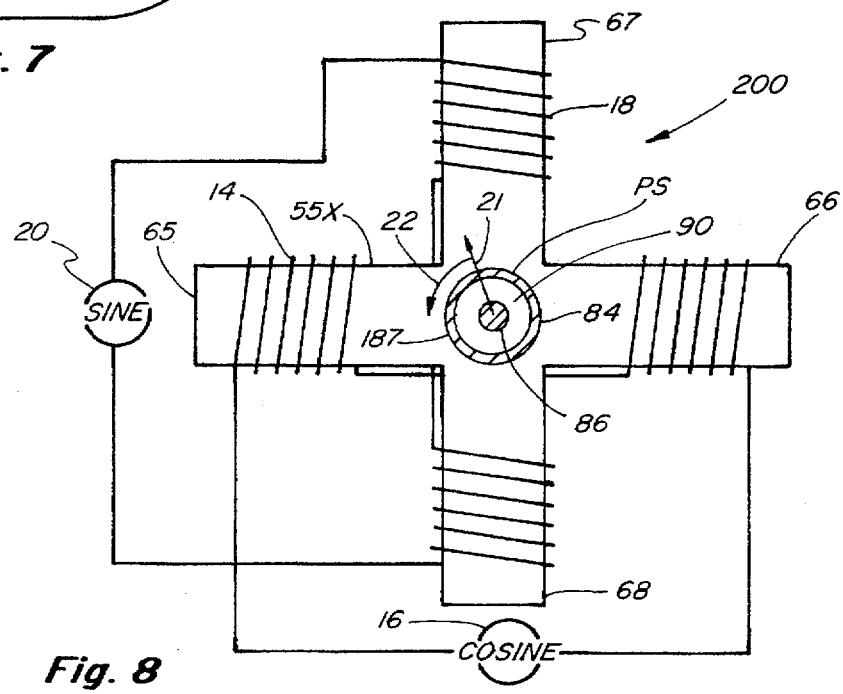
*Fig. 7*
*Fig. 8*

DRIVING CORES FOR POLAR COORDINATES SENSORS

RELATED PATENT APPLICATIONS

This application is a continuation-in-part of application Ser. No. 08/142,933 filed Oct. 29, 1993, now U.S. Pat. No. 5,532,591; application Ser. No. 08/187,072 filed Jan. 27, 1994, now U.S. Pat. No. 5,574,367; application Ser. No. 08/217,738 filed Mar. 25, 1994, now U.S. Pat. No. 5,554,933; application Ser. No. 08/267,511 filed Jun. 29, 1994, now U.S. Pat. No. 5,559,432; application Ser. No. 08/388,825 filed Feb. 15, 1995, now U.S. Pat. No. 5,548,212; application Ser. No. 08/599,775 filed Feb. 12, 1996. Also Disclosure Document Nos. 371371, filed Feb. 3, 1995, 387120 and 401663 filed Jun. 17, 1997.

BACKGROUND OF THE INVENTION

1. Field of the Invention

The pick-up elements (polar sensors) disclosed in the above patent applications are magnetically driven by a rotating field within a hollow toroid core. Some of the accompanying problems with conducting the driving flux within the hollow toroid to the workpiece have been: (a) the flux path between the driving toroid and the pick-up core i.e. unwanted reluctance due to a poor fit of the pick-up core in the mounting bore machined in the hollow toroid wall. (b) the hollow toroid separation line for assembling the driving core is usually in the outer circumference where the mounting bore is formed, this also is an unwanted reluctance.

SUMMARY OF THE INVENTION

The present invention discloses several driving core embodiments providing improvement in coupling the driving field to the pick-up core (polar sensor).

Disclosed is a method of forming the pick-up core as an integral part of the driving core to eliminated flux gaps. Also disclosed is an elongated hollow toroid driving core in which the driving core couples evenly around the pick-up core element for a more uniform sensing pattern.

The disclosed embodiments of rotating field cores are for driving the above enumerated polar coordinates sensor inventions e.g. single-phase polar sensor, poly-phase polar sensor, polar sensing array.

A cross shaped driving core is disclosed providing two rotating field areas for driving polar coordinate sensors. By combining a modified hollow toroid driving core with a modified cross shaped driving core a unique dual rotating field polar coordinate sensor is provided.

Both circular (balanced sine-cosine excitation) and precessing elliptical (unbalanced sine-cosine excitation) modes and frequency modulated (e.g. ramp and sine waveforms) excitation modes, all may be used to excite the driving cores of this disclosure.

POLAR COORDINATES SENSOR BASICS

FIG. 1 is an isometric view of a rotating magnetic field source comprising a hollow toroid core 55 formed of a ferromagnetic material, an inside excitation winding 58 and an outside excitation winding 62. Sine-cosine voltages are connected to windings 58, 62 inducing a rotating magnetic field coextensive throughout core 55. FIG. 2 is a cross-sectional view of core 55, dimensions A, B, C, D, being approximately equal for uniform distribution. The generic polar coordinates sensor (polar sensor) is shown in isometric view in FIG. 3. Polar sensor (PS) comprises a pick-up core 88 formed of high permeability ferromagnetic material and a pick-up coil 90. Central pole 86 is concentrically surrounded by an outer cylindrical pole 84 and spaced apart to provide an annular pick-up coil space 89, these two poles are connected at one end by a base portion 85. The annular open end is the sensing face and is referenced in azimuth degrees for conveniece, the rotating sensing pattern revolves around the Z-axis. The Z-axis of pick-up core 88 is perpendicular to the central axis CA (FIG. 5) of driving core 55. Field rotational direction at four core wall locations on the Z-axis are labeled by CCWF and CCW.

Pick-up coil 90 is wound around central pole 86 having connecting leads 39. The output signal from pick-up coil 90 indicates target direction by phase angle and target size and or azimuth distance by amplitude level. Referring to FIGS. 4, 5 polar sensor PS is mounted in a bore 87 formed in the outer circumference wall of driving core 55, this disposing the Z-axis of the pick-up core 88 perpendicular to a plane drawn tangent to the core surface. This also disposes the plane of pick-up coil 90 coplanar to the driving flux lines, and with no target (workpiece) present there is no net flux linkage to pick-up coil 90. Coplanar driving has inherent advantages over an axial driven pick-up coil e.g. signal null when sensing pattern is balanced, the generated signal may contain frequencies higher and or lower than the excitation frequency (unfiltered signal).

FIG. 5 is a central axis CA view of driving core 55 showing the driving flux (FLUX) path is from driving core 55 through the outer cylindrical pole 84, through the base portion 85 up through the central pole 86, through the FERROUS TARGET, down through the outer cylindrical pole 84 and back to driving core 55.

The coplanar disposition of pick-up coil 90 and the quasi-driven central pole 86 allow frequencies different from the sine-cosine excitation frequency to be generated in pick-up coil 90.

BRIEF DESCRIPTION OF THE INVENTION

FIG. 6 is the first embodiment of a driving core, an elongated hollow toroid.

FIG. 7 is a cross-section of an elongated hollow toroid driving core having an integral pick-up core.

FIG. 8 is the second embodiment of a driving core having a cross shaped structure.

DETAILED DESCRIPTION OF THE INVENTION ELONGATED DRIVING CORE EMBODIMENT

Figure 1:
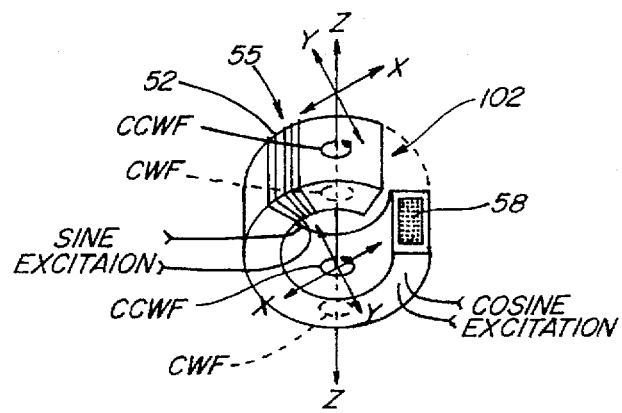
FIG. 1 is a hollow toroid, an earlier driving core for polar coordinate sensors.
Figure 2:
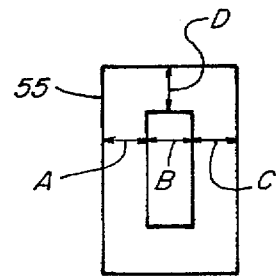
FIG. 2 is a cross-section view of the hollow toroid in FIG. 1.
Figure 3:
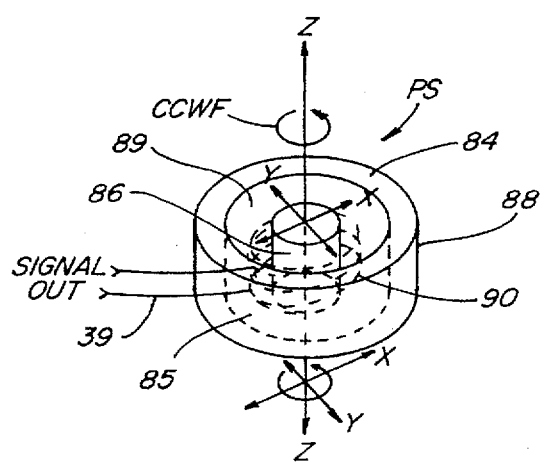
FIG. 3 illustrates the elements of a basic polar coordinates sensor.

The polar sensor devices disclosed in the listed related Patents, Patent Applications, and Disclosure Documents may be improved e.g. spatial resolution and greater sensing flux strength by modifications to the hollow toroid driving core.

FIG. 6, 7, show embodiment 100 of an elongated (flattened) hollow toroid driving core. A hollow toroid core having elongated sides and end caps was disclosed in U.S. Pat. No. 4,595,843. There is an outside excitation winding 62 (FIG. 6) and an inside excitation winding 58 (FIG. 7). Sine-cosine excitation being applied to excitation windings 62, 58, to induce a rotating magnetic field through the entire core. There are two modifications included in the driving core embodiment 100 shown in FIG. 6 (isometric view) i.e. (1) the hollow toroid 155 is flattened to provide better flux coupling to the outer cylindrical pole 184, the flattened portion 94. The extending portion 95 of outer cylindrical pole 184 is of equal length 360 degrees around the circumference providing a more uniform sensing pattern. (2) The integral polar sensor element IPS is formed as an integral part of driving core 155 thus eliminating poor fit problems, this is better seen in FIG. 7. The integral polar sensor element IPS has a central pole 186, around which is wound a pick-up coil 190 with connecting leads 191. The annular pick-up coil space 183 extends approximately 50 percent of the way through the driving core wall thickness, the remaining portion of the wall thickness becomes a base portion 185. As in the generic version, the central pole axis is disposed perpendicular to the driving core surface (flattened portion 94) and pick-up coil 190 is disposed coplanar to the driving flux.

Referring again to FIG. 6, driving core 155 may have a separable portion 192 in the form of a lid having a separation line (dotted line) 193 for assembling pick-up coil 190 inside.

The complete integral driving core may be molded and machined utilizing well known pot core technology.

CROSS SHAPED DRIVING CORE EMBODIMENT

Figure 4:
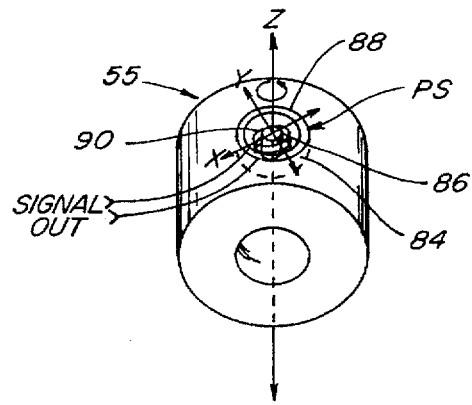
FIG. 4 shows a polar coordinate sensor mounted in the wall of a hollow toroid driving core.
Figure 5:
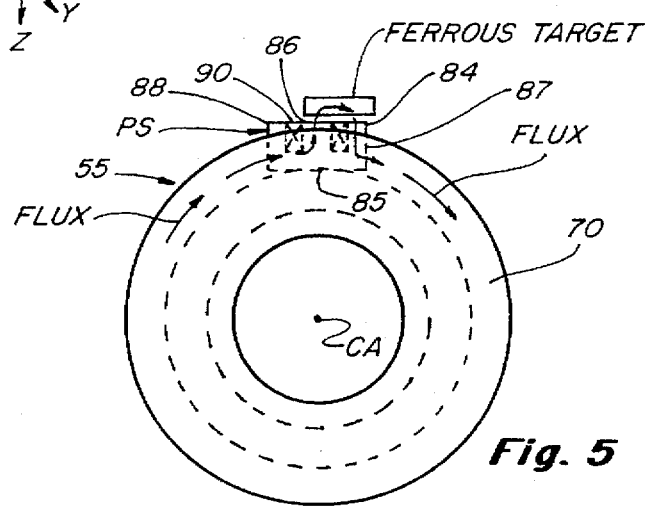
FIG. 5 shows the driving flux path coupling a ferrous target.
Figure 9:
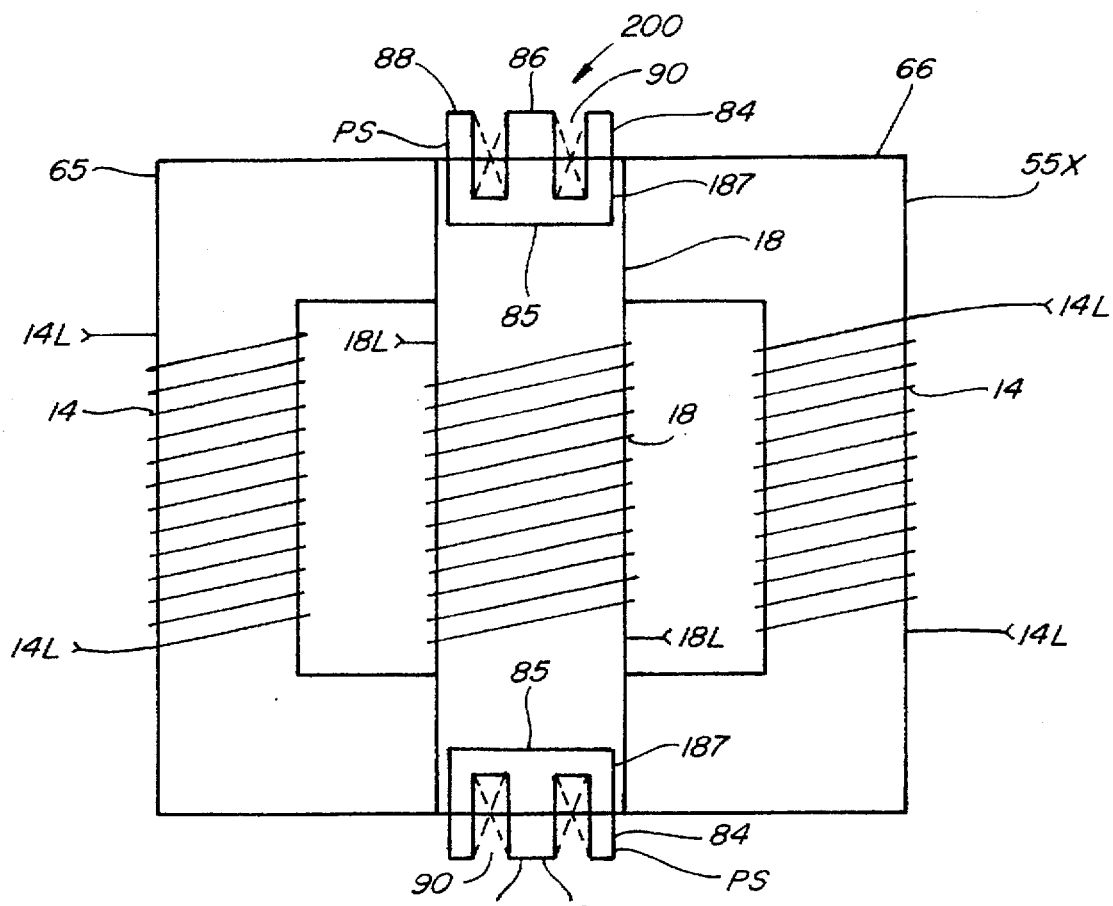
FIG. 9 is a side view of a polar sensor driven by a cross shaped core.

The DelVecchio et al. U.S. Pat. No. 4,595,843 disclosed a magnetic core in the shape of a cross with flux return yokes, this type of core being illustrated in FIG. 8 (yokes not shown). In this second embodiment 200 of a driving core, utilization is made of the the rotating magnetic field created where the core arms intersect. The polar sensor device 200 in FIG. 8 comprises an excitation winding 14 wound around first and second arms 65, 66, of core 55X and connected to a cosine voltage source 16. The device 200 also includes an excitation winding 18 wound around third and forth arms 67, 68, and connected to a sine voltage source 20. The induction in the center of core 12 is the vector sum of the indictions produced by windings 14 and 18. If the two excitation sources are 90 degrees out of phase and are of equal peak magnitude and the windings 14, 18 have equal number of turns, the resultant induction vector 21, in the center of the core 55X traces out a circle 22 as it rotates with time. By machining a bore 187 in the cross center (intersection of arms 65, 66, 67, 68) of core 55X, and mounting a polar sensor partialy with this bore, we again have a driven polar sensor as in FIGS. 4, 5. The mounted polar sensor (PS) may take the form of any one of the polar sensor devices described in the listed related patents and filed disclosures. Alternately the pick-up core may take the form of an integral pick-up core as driving core embodiment 100 in FIGS. 6, 7. Although polar sensing device 200 has only two rotating field portions (where the two sine-cosine magnetic circuits intersect, at the top and bottom of the connecting yokes, FIG. 10) nevertheless it may be used for the same purpose as the hollow toroid embodiment. FIG. 9 is a side view of driving core 55X, showing two mounted polar sensors, one at the top and one at the bottom. Excitation winding 14 comprises a coil wound around arms 65, 66, having connecting leads 14L and excitation winding 18 comprises two coils wound around arms 67, 68, having connecting leads 18L. According to the DelVecchio et al. Patent col. 2 lines 44-62, when sine-cosine excitation is applied to these two excitation windings (14, 18) a rotating magnetic field will exist in the yoke intersection.

This cross shaped driving core 55X may be used to drive all the polar sensors e.g. single-phase, poly-phase, polar sensing array, and conical sensing face, embodiments. The method for generating a rotating elliptical sensing pattern as disclosed in pending patent application Ser. No. 08/599,775 may also be used with device 200. Cross shaped driving core 55X may be made separable for assembly. In FIGS. 8, 9, the polar sensor PS comprises a pick-up core 88 formed of ferromagnetic material, a pick-up coil 90, (connecting leads not shown), a central pole 86, an outer cylindrical pole 84, and a base portion 85.

This field intersection principle may be extended to include almost any number of arms intersecting at a point e.g. 3 arms utilizing 3 phase excitation and 5 arms utilizing 5 phase excitation to generate a rotating magnetic field. This type of pole arrangement is similar to poly-phase induction motor stator designs for generating rotating magnetic fields.

HOLLOW TOROID AND CROSS SHAPED DRIVING CORE COMBINATION

Figure 10:
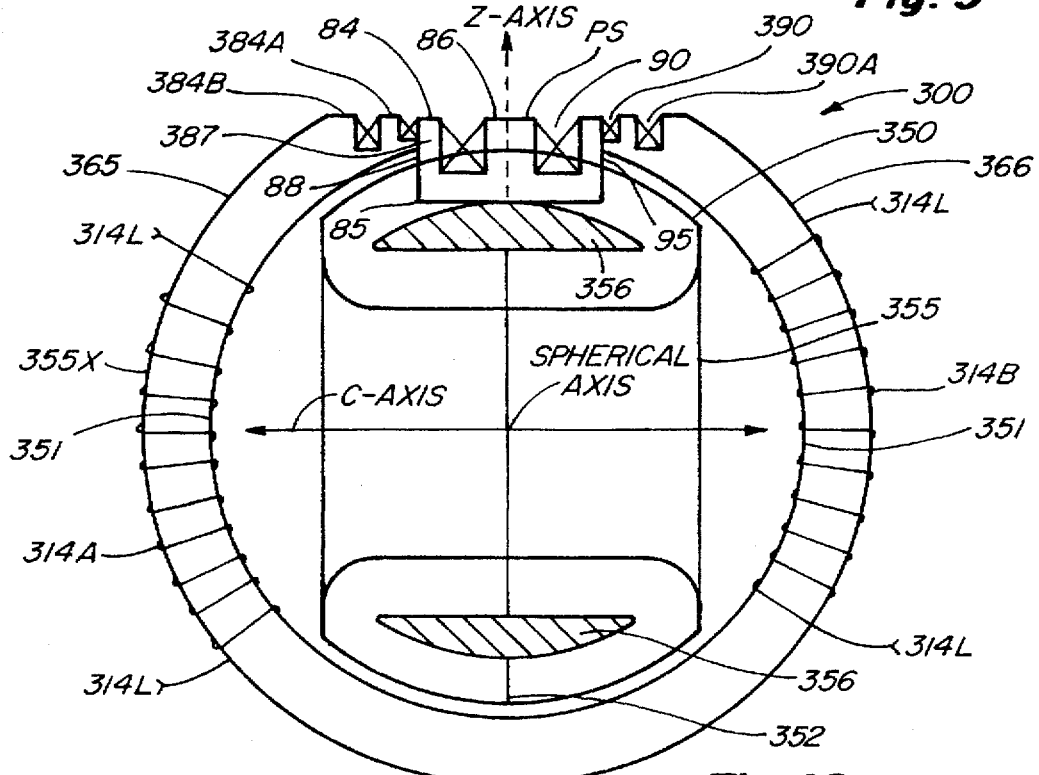
FIG. 10 is a polar coordinate sensor combination comprising a hollow toroid driving core and a cross shaped driving core.
Figure 11:
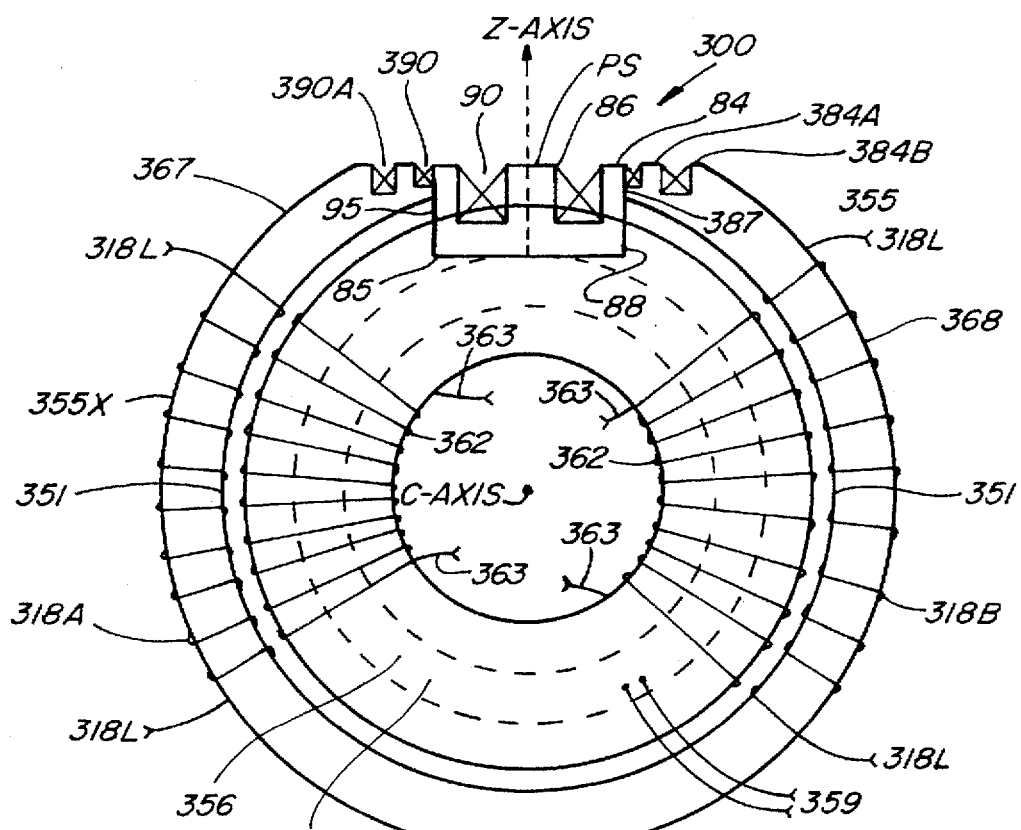
FIG. 11 is another view of the polar sensor combination in FIG. 10.
Figure 12:
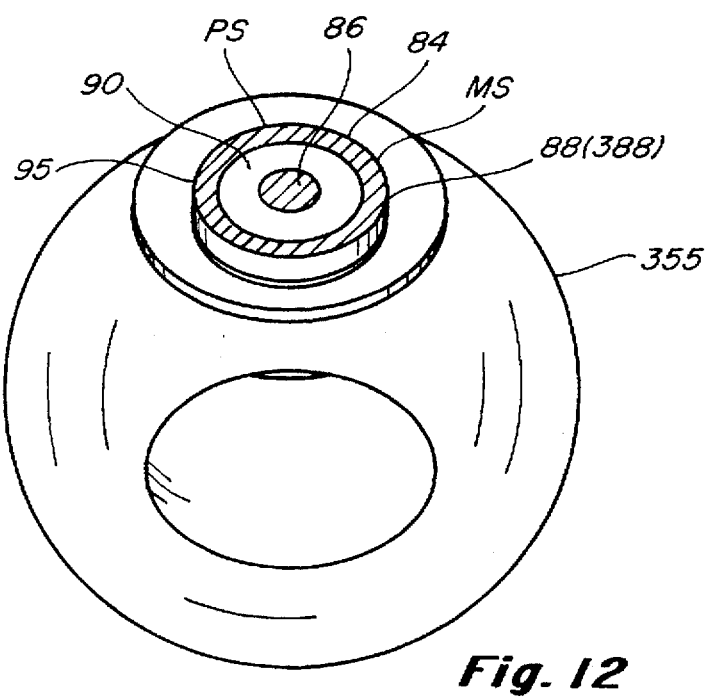
FIG. 12 is a polar coordinates sensor driven by a hollow toroid having a spherical shaped outer circumference.
Figure 13:
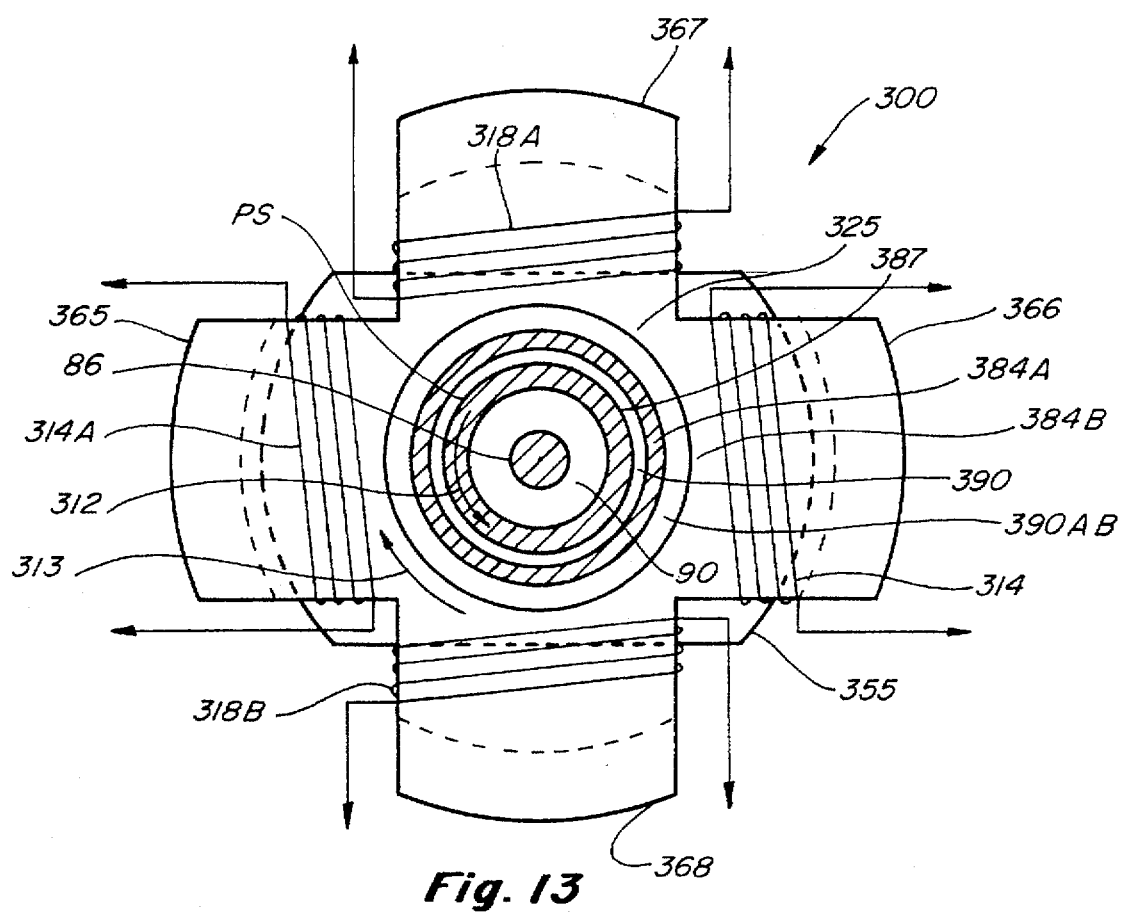
FIG. 13 is a radial view of the concentric pick-up assembly provided by the dual driving core device in FIGS. 10, 11.

By combining a modified hollow toroid driving core with a modified cross shaped driving core a dual rotating field polar sensor 300 is provided as shown in FIGS. 10, 11, 13. A bore 387 is formed in the center of the core arms of the modified cross shaped driving core 355X intersect. Bore 387 fits around the extending portion of a polar sensor mounted or formed on the outer circumference of the modified hollow toroid driving core 355. This dual driving core arrangement provides two concentric interacting rotating magnetic fields. Referring now to FIG. 11, which is a central axis (C-axis) view of a hollow toroid driving core 355, having an inside excitation winding 356 with connecting leads 359 and an outside toroidal excitation winding 362 (comprising two sub-windings) with connecting leads 363. The device in FIGS. 11, 12, comprises a hollow toroid driving core 355 inclosed by a cross shaped driving core 355X. As shown in FIGS. 10, 11, cross shaped driving core 355X may be made separable on lines 351. In FIGS. 10, 13, excitation sub-windings 314A and 314B are wound around core arms 365 and 366 respectfully. In FIGS. 11, 13, excitation sub-windings 318A and 318B are wound around core arms 367 and 368 respectfully. The hollow space for the inside excitation winding 356 is shown in FIG. 11. Referring again to FIGS. 10, 11, we see hollow toroid driving core 355 has a D shaped cross-section i.e. the outer circumference cross-section is spherical shape i.e. every point on the outer circumference being equidistant from the SPHERICAL AXIS. Driving core 355 is formed of a high permeability ferromagnetic material and is made separable on line 352 (the Z-axis of the mounted polar sensor). Polar sensor PS is located on this spherical shaped core wall with an extending portion 95 beyond the driving core surface. The Z-axis of polar sensor PS is perpendicular to the central axis (C-axis) of driving core 355. The spherical shaped outer circumference provides a more uniform driving flux coupling to the mounted polar sensor PS i.e. the driving core 355 coupling to the pick-up core 88 is the same height 360 degrees around the outer cylindrical pole 84. The spherical shaped outer circumference also allows the cross shaped driving core 355X to fit more compactly. FIG. 12 is a isometric view of driving core 355 further illustrating the spherical shaped outer circumference. The pick-up core 88 (388) may be formed as an integral part of driving core 355 like in the elongated driving core embodiment of FIGS. 6, 7. Shown also in FIG. 12 is a magnetic shield MS concentrically surrounding the extending portion 95 of pick-up core 388. Magnetic shield MS is formed of a non-ferrous material such as copper having a spherical shape to conform to the spherical contour of driving core 355. The purpose of Magnetic shield MS is to block any driving flux leakage that might distort the sensing pattern.

Obviously the polar sensor PS-driving core 355 combination may be used without the cross shaped outer driving core 355X (FIGS. 10, 11). The cross shaped driving core 355X is similar to the one shown in FIG. 9, the difference being the legs 365, 366, 367, 368, have a curved shape (curved in both longitudinal and radial directions) to reduce the flux circuit lengths and provide a more compact sensing device. Driving cores 355, 355X, may be held in relative position by means of a rigid insulating material such as Epoxy. Driving core 355 is excited by sine-cosine excitation through connecting leads 363 and 359 as described for driving core embodiment 100. Driving core 355X is also excited by sine-cosine excitation via connecting leads 314L and 318L as described in the cross shaped driving core 200 to induce a rotating magnetic field at the top and bottom (the two intersection portions) 325 as illustrated by curved arrow 313 in FIGS. 13, 14.

Figure 14:
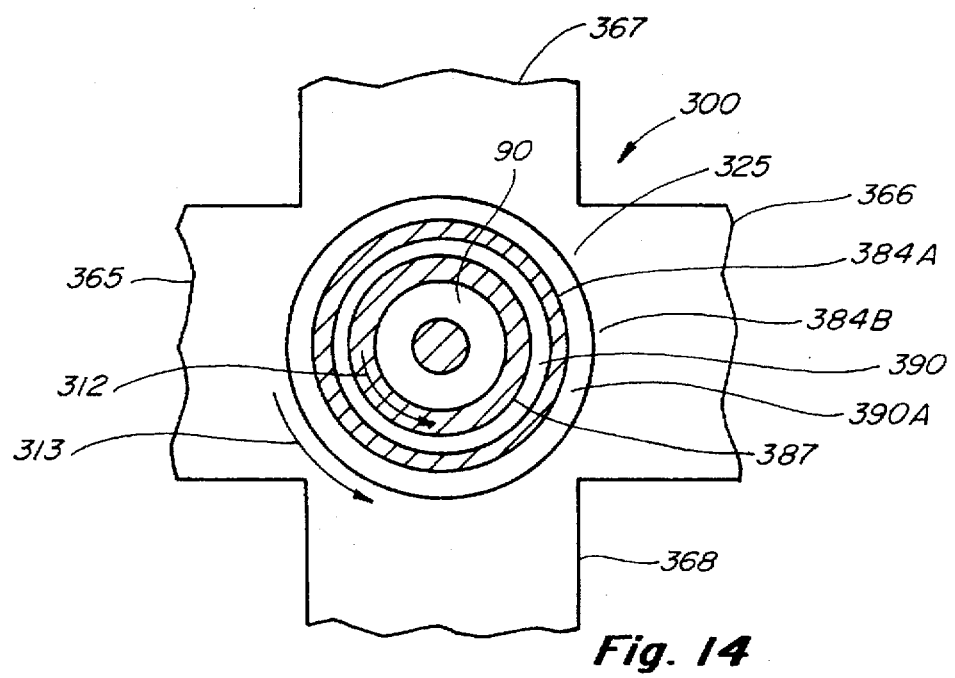
FIG. 14 illustrates sensing pattern rotational direction of dual driving cores.

This dual driving core embodiment may also have a plurality of concentric pick-up coils wound in concentric grooves formed in the flattened area concentric to bore 387 for generating additional polar coordinate signals. Referring again to FIGS. 10, 11, there is shown two concentric pick-up coils 390, 390A, wound in two concentric grooves formed in the top intersection portion of cross shaped driving core 355X. Pick-up coil 390 is wound around the cylindrical outer pole 84 of polar sensor PS. Pick-up coil 390A is wound around an annular intermediate pole 384A. There is an outer annular pole 384B. FIG. 13 is a top view of the dual rotating field polar sensor 300 showing the concentric structure. Two sine-cosine generators may be used to excite device 300, one for the hollow toroid driving core and one for the cross shaped driving core. As an alternative a single sine-cosine generator would suffice (field rotation rates being equal). Field rotational directions 312,313 may be ccw-cw as shown in FIG. 13 or they may be ccw-ccw as shown in FIG. 14. If the fields rotate in opposite directions at the same speed there will be an additive dipole and a subtractive dipole generated for each revolution. By adjusting the phase of the first field ahead of, or behind the second field a steerable (both ccw and cw) sensing pattern may be produced. The steering sensing azimuth range is 360 degrees. Both fields may rotate in the same direction, but one faster than the other to produce a beacon type of scanning pattern. The sine-cosine excitation modes e.g. field direction and frequency (speed) may be stored in digital memory to be read into digital-to-analog converters.

Figure 15:
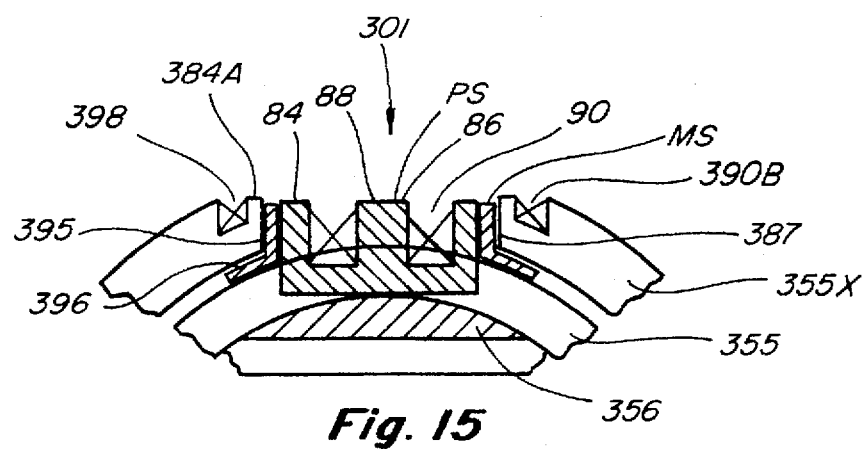
FIGS. 15, 16 illustrate a second embodiment of concentric pick-up assembly for use with the dual driving core device of FIGS. 10, 11.
Figure 16:
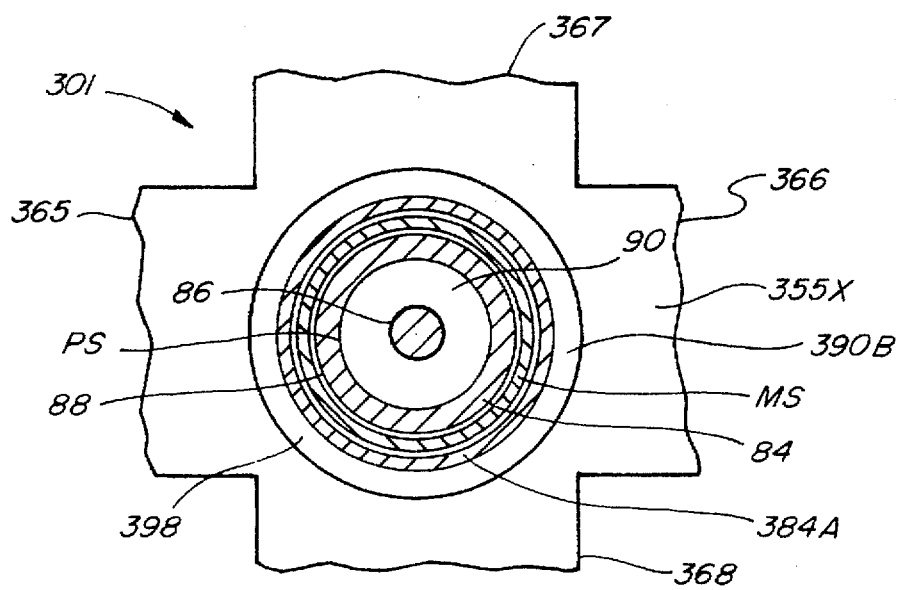

FIGS. 15, 16, show a second embodiment of pick-up coil arrangement of a dual field sensor 301. FIG. 15 is a cross-section view of hollow toroid driving core 355 showing the inside excitation winding 356 and the cross shaped driving core 355X. Sensor 301 has a polar sensor PS mounted in the spherical shaped outer circumference of driving core 355. Concentrically surrounding the extending portion (portion of pick-up core 88) is a magnetic shield formed of a nonferrous material such as copper. Magnetic shield MS has a cylindrical portion 395 and a concave portion 396 to conform to the spherical circumference of driving core 355. There is a bore 384A formed in an intersection of cross shaped driving core 355X. Bore 384A concentrically surrounds the cylindrical portion 395 of magnetic shield MS. Referring to FIG. 16, there is a groove 398 formed in driving core 355 and is concentric around polar sensor PS. Within groove 398 is wound pick-up coil 390B. Sensor embodiment 301 may be excited by the same excitation modes given for the dual field sensor 300 embodiment.

I claim:

1. An integrally formed hollow toroid driving core and pick-up core combination for generating a polar coordinates signal in a pick-up coil; said combination comprising:
   a) a hollow toroid core formed of a high permeability material having oval shaped outer and inner diameters, there being two flattened portions on the outer circumference of the hollow toroid;
   b) the integrally formed pick-up core being a raised portion in the center of one of the two flattened portions; the said raised portion further comprising:
      i) an annular shaped outer pole;
      ii) an annular shaped pick-up coil space formed concentric within the annular shaped outer pole; the depth of the said pick-up coil space extending into the driving core wall, leaving a cylindrical central pole, the remaining core wall thickness forming a pick-up core base portion;
      iii) a pick-up coil wound around the said central pole for generating a polar coordinates signal.

2. A combination of a polar coordinates sensor driven by a cross shaped driving core, said combination comprising:
   a) a driving core formed of a high permeability magnetic material; further comprising:
      i) first and second rectangular shaped cores being orthogonally connected on a common axis to form first and second core intersections;
      ii) a bore formed in the said first and second core intersections for mounting a polar coordinates sensor, the axis of each bore being on the said common axis;
      iii) a polar coordinates sensor being mounted partially within one of the said bores, leaving a sensing portion extending outside the driving core surface;
      iv) a first excitation winding being wound around the first rectangular shaped core for inducing a first closed magnetic field;
      v) a second excitation winding being wound around the second rectangular shaped core for inducing a second closed magnetic field;

vi) sine-cosine excitation being applied to the first and second excitation windings for inducing a rotating magnetic field in the first and second core intersections for driving the said polar coordinates sensor, the winding turns of the said pick-up coil being coplanar to the driving flux lines, a balanced sensing pattern generating a signal null.

3. The invention according to claim 2, wherein the said polar coordinates sensor is formed as an integral part of the driving core.

4. A dual rotating field sensor having multiple pick-up coils driven by a combination of a spherical hollow toroid driving core and a modified cross shaped driving core, for generating a plurality of polar coordinates signals, each generated signal containing independent phase and amplitude information, said sensor comprising:

a) a spherical hollow toroid driving core formed of a high permeability magnetic material for generating a first driving field, the hollow toroid having a D shaped cross-section with every point on the outer circumference being equidistant from a spherical axis at the center of the hollow toroid, forming a spherical shaped outer circumference;

a lesser bore being formed on the spherical shaped outer circumference for mounting a polar coordinates sensor, the lesser bore axis being centered on the spherical axis;

a first polar coordinates sensor having a first pick-up coil, being mounted partially within the said lesser bore leaving an extending sensing portion outside the toroid surface, said first polar coordinates sensor for generating a first polar coordinates signal;

a first excitation winding wound within the hollow toroid driving core for inducing a first magnetic field throughout the hollow toroid driving core;

a second excitation winding wound around the hollow toroid driving core for inducing a second magnetic field throughout the hollow toroid driving core, the winding turns being wound symmetrically to the mounted polar coordinates sensor for driving flux balance;

b) the said modified cross shaped driving core being formed of a high permeability magnetic material for generating a second driving field; the configuration of the said modified cross shaped driving core further comprising:

i) first and second circular shaped cores linked together at first and second diametral intersections forming two orthogonal magnetic circuits; and ii) a first excitation winding wound around the first circular shaped core for inducing a first orthogonal field;

iii) a second excitation winding wound around the second circular shaped core for inducing a second orthogonal field;

iv) sine-cosine excitation being applied to the first and second excitation windings for inducing a rotating magnetic field in the said diametral intersections;

v) a greater bore formed in the center of the first diametral intersection, the axis of said greater bore being on a line passing through the center of the second diametral intersection;

vi) the modified cross shaped driving core enclosing the spherical hollow toroid driving core, the greater bore being disposed coaxially with the said lesser bore and with the greater bore being disposed in a concentric sensing face around the extending sensing portion of the polar coordinates sensor mounted in the spherical hollow toroid driving core, leaving an annular second pick-up coil space; and vii) a second pick-up coil being wound around the outside of the said extending sensing portion for generating a second polar coordinates signal;

viii) the rotating fields generated by the two driving cores concentrically combining in the said concentric sensing face for generating a resultant sensing pattern having two concentric interacting rotating fields dependent on the frequency, phase and amplitude of a plurality of predetermined sine-cosine excitation combinations applied to the respective excitation windings of the said two driving cores.

5. The invention according to claim 4, wherein the said resultant sensing pattern is generated by the said interacting rotating fields moving at the the same angular velocity and direction for a greater sensing field strength.

6. The invention according to claim 4, wherein the said resultant sensing pattern is generated by the said interacting rotating fields moving at the same angular velocity in opposite directions for additive and subtractive dipole effects in the sensing pattern.

7. The invention according to claim 4, wherein the said resultant sensing pattern is generated by the said interacting rotating fields moving at predetermined different angular velocities and directions for steerable dipole effects in the sensing pattern.

* * * * *